US011590087B2

United States Patent
Guy et al.

(10) Patent No.: US 11,590,087 B2
(45) Date of Patent: Feb. 28, 2023

(54) CANNABIDIOL-TYPE CANNABINOID COMPOUND

(71) Applicant: GW Research Limited, Cambridge (GB)

(72) Inventors: Geoffrey Guy, Cambridge (GB); Volker Knappertz, Cambridge (GB); Benjamin Whalley, Cambridge (GB); Marie Woolley-Roberts, Cambridge (GB)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 17/743,653

(22) Filed: May 13, 2022

(65) Prior Publication Data

US 2022/0265573 A1    Aug. 25, 2022

Related U.S. Application Data

(63) Continuation of application No. PCT/GB2020/052944, filed on Nov. 18, 2020.

(30) Foreign Application Priority Data

Nov. 21, 2019    (GB) ...................... 1916977

(51) Int. Cl.
*A61K 31/05* (2006.01)
*A61P 25/08* (2006.01)
*C07C 37/00* (2006.01)

(52) U.S. Cl.
CPC .............. *A61K 31/05* (2013.01); *A61P 25/08* (2018.01); *C07C 37/00* (2013.01)

(58) Field of Classification Search
CPC ..................................................... A61K 31/05
See application file for complete search history.

(56) References Cited

U.S. PATENT DOCUMENTS

| | | | |
|---|---|---|---|
| 6,630,507 B1 | 10/2003 | Hampson et al. |
| 9,474,726 B2 | 10/2016 | Guy et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,092,525 B2 | 10/2018 | Guy et al. |
| 10,111,840 B2 | 10/2018 | Guy et al. |
| 10,137,095 B2 | 11/2018 | Guy et al. |
| 10,583,096 B2 | 3/2020 | Guy et al. |
| 10,603,288 B2 | 3/2020 | Guy et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,765,643 B2 | 9/2020 | Guy et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Wright et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |
| 2014/0298511 A1 | 10/2014 | Lewis et al. |
| 2015/0359756 A1 | 12/2015 | Guy et al. |
| 2017/0239193 A1 | 8/2017 | Guy et al. |
| 2018/0071210 A1 | 3/2018 | Wilkhu et al. |
| 2018/0228751 A1 | 8/2018 | Stott et al. |
| 2019/0167583 A1 | 6/2019 | Shah |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |

(Continued)

FOREIGN PATENT DOCUMENTS

GB    2 527 599 A    12/2015

OTHER PUBLICATIONS

Kimball, A. W. et al., "Chemical Protection against Ionizing Radiation," Radiation Research, 7:1-12 (1957).
Lander, N. et al., "Total synthesis of cannabidiol and delta1-tetrahydrocannabinol metabolites," Journal of the Chemical Society, Perkin Transactions 1, Royal Society of Chemistry, pp. 8-16, 1976.
Lewis, M. M. et al., "Chemical Profiling of Medical Cannabis Extracts," ACS Omega, 2:6091-6103 (2017).
Swinyard, E. A. & Kupferberg, H. J., "Antiepileptic drugs: detection, quantification, and evaluation," Federation Proc. 44:2629-2633 (1985).
Ujváry, I. & Hanus, L., "Human Metabolites of Cannabidiol: A Review on Their Formation, Biological Activity, and Relevance in Therapy," Cannabis and Cannabinoid Research, 1(1) (2016), 12 pages; doi:10.1089/can.2015.0012.
U.S. Appl. No. 15/640,033, filed Jun. 30, 2017.

(Continued)

*Primary Examiner* — Yong S. Chong
(74) *Attorney, Agent, or Firm* — Cooley LLP

(57) ABSTRACT

The present invention relates to a cannabidiol (CBD) type cannabinoid compound for use as a medicament. The CBD-type cannabinoid, 6-hydroxy cannabidivarin (6-OH CBDV), is a metabolite of cannabidivarin (CBDV). The cannabinoid can be produced by synthetic means and a method for the production of 6-OH CBDV is described herein. In addition, disclosed herein are data which demonstrate the efficacy of 6-OH CBDV in a model of disease.

20 Claims, 1 Drawing Sheet

(56) References Cited

U.S. PATENT DOCUMENTS

| | | |
|---|---|---|
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0330636 A1 | 10/2021 | Guy et al. |
| 2022/0000800 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0096397 A1 | 3/2022 | Wright et al. |
| 2022/0168266 A1 | 6/2022 | Guy et al. |
| 2022/0184000 A1 | 6/2022 | Guy et al. |
| 2022/0202738 A1 | 6/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |

OTHER PUBLICATIONS

U.S. Appl. No. 16/467,639, filed Jun. 7, 2019.
U.S. Appl. No. 16/624,106, filed Dec. 18, 2019.
U.S. Appl. No. 16/737,707, filed Jan. 8, 2020.
U.S. Appl. No. 16/764,701, filed May 15, 2020.
U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 17/025,130, filed Sep. 18, 2020.
U.S. Appl. No. 17/050,956, filed Oct. 27, 2020.
U.S. Appl. No. 16/935,005, filed Jul. 21, 2020.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/470,382, filed Sep. 9, 2021.
U.S. Appl. No. 17/472,000, filed Sep. 10, 2021.
U.S. Appl. No. 17/472,016, filed Sep. 10, 2021.
U.S. Appl. No. 17/548,232, filed Dec. 10, 2021.
U.S. Appl. No. 17/477,172, filed Sep. 16, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/615,422, filed Nov. 30, 2021.
U.S. Appl. No. 17/552,487, filed Dec. 16, 2021.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/680,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/786,949, filed Jun. 17, 2022.
U.S. Appl. No. 17/819,046, filed Aug. 11, 2022.

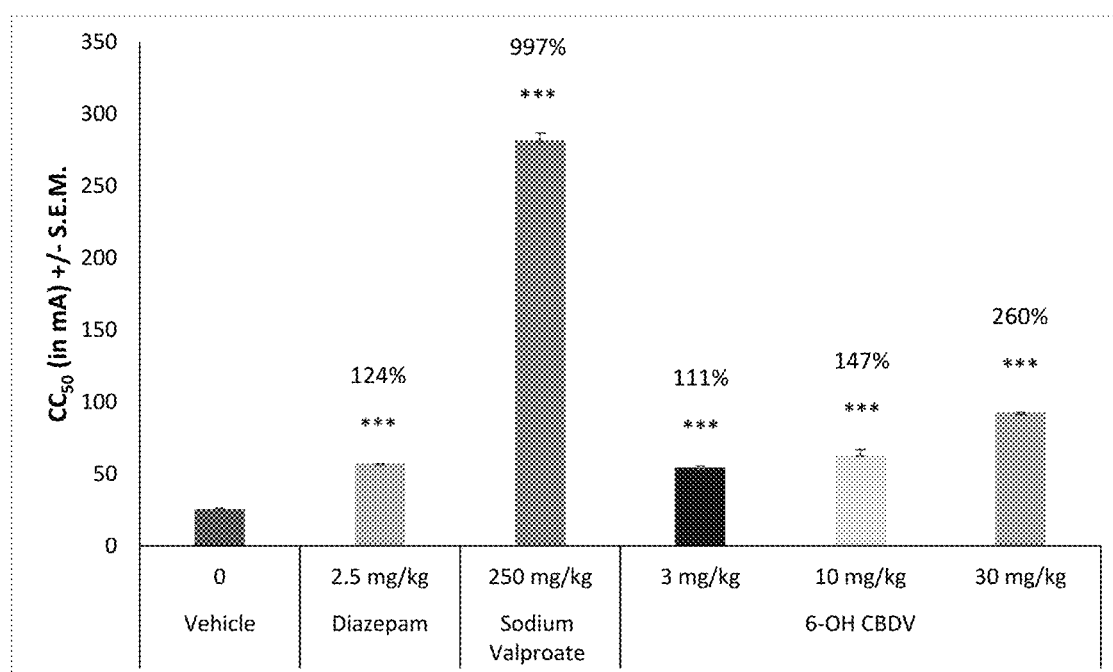

CANNABIDIOL-TYPE CANNABINOID COMPOUND

CROSS-REFERENCE TO RELATED APPLICATIONS

This application claims the benefit of International PCT Application No. PCT/GB2020/052944, filed Nov. 18, 2020, and United Kingdom Application No. 1916977.0, filed Nov. 21, 2019. Each of the aforementioned applications are incorporated herein by reference in its entirety.

FIELD OF THE INVENTION

The present invention relates to a cannabidiol (CBD) type cannabinoid compound for use as a medicament.

The CBD-type cannabinoid, 6-hydroxy cannabidivarin (6-OH CBDV), is a metabolite of cannabidivarin (CBDV). The cannabinoid can be produced by synthetic means.

Disclosed herein are data which demonstrate the efficacy of 6-OH CBDV in a model of disease. In addition, a method for the production of 6-OH CBDV is described.

BACKGROUND TO THE INVENTION

Cannabinoids are natural and synthetic compounds structurally or pharmacologically related to the constituents of the cannabis plant or to the endogenous agonists (endocannabinoids) of the cannabinoid receptors CB1 or CB2. The only way in nature in which these compounds are produced is by the cannabis plant. Cannabis is a genus of flowering plants in the family Cannabaceae, comprising the species *Cannabis sativa*, *Cannabis indica*, and *Cannabis ruderalis* (sometimes considered as part of *Cannabis sativa*).

Cannabis plants comprise a highly complex mixture of compounds. At least 568 unique molecules have been identified. Among these compounds are cannabinoids, terpenoids, sugars, fatty acids, flavonoids, other hydrocarbons, nitrogenous compounds, and amino acids.

Cannabinoids exert their physiological effects through a variety of receptors including, but not limited to, adrenergic receptors, cannabinoid receptors (CB1 and CB2), GPR55, GPR3, or GPR5. The principle cannabinoids present in cannabis plants are cannabinoid acids Δ9-tetrahydrocannabinolic acid (Δ9-THCA) and cannabidiolic acid (CBDA) with small amounts of their respective neutral (decarboxylated) cannabinoids. In addition, cannabis may contain lower levels of other minor cannabinoids. "Chemical composition, pharmacological profiling, and complete physiological effects of these medicinal plants, and more importantly the extracts from cannabis, remain to be fully understood." Lewis, M. M. et al., ACS Omega, 2, 6091-6103 (2017).

Crude extracts from cannabis plants containing CBD have been used by patients suffering from diseases and disorders. However, such crude products are unsuitable for use in pharmaceutical formulations. Those seeking to prepare more consistent CBD preparations for use in treating diseases or disorders have made a concerted effort to either prepare CBD synthetically or attempt to remove all compounds other than CBD, particularly psychoactive compounds such as THC, from plant derived cannabinoids. See for example US 2014/0298511.

The present invention encompasses the surprising discovery that a metabolite of CBDV has therapeutic efficacy. This compound, 6-hydroxy cannabidivarin (6-OH CBDV) can be produced synthetically and may be used in a purified form.

Cannabinoids are a class of compounds which many of which can be derived naturally from the cannabis plant or produced synthetically via chemical synthesis.

More than 100 different cannabinoids produced by cannabis have been identified. These cannabinoids can be split into different groups as follows: phytocannabinoids; endocannabinoids and synthetic cannabinoids (which may be novel cannabinoids or synthetically produced versions of phytocannabinoids or endocannabinoids).

Phytocannabinoids are cannabinoids that originate from nature and can be found in the cannabis plant. Phytocannabinoids can be isolated from plants to produce a highly purified extract. Phytocannabinoids may be obtained as either the neutral (decarboxylated form) or the carboxylic acid form depending on the method used to extract the cannabinoids from plant material. For example, it is known that heating the carboxylic acid form will cause most of the carboxylic acid form to decarboxylate into the neutral form. Phytocannabinoids can only be produced from plants, however versions of phytocannabinoids may be produced synthetically via chemical synthesis.

Endocannabinoids are endogenous lipid-based retrograde neurotransmitters that bind to cannabinoid receptors, and cannabinoid receptor proteins that are expressed throughout the mammalian central nervous system (including the brain) and peripheral nervous system. The endocannabinoid system is involved in regulating a variety of physiological and cognitive processes including fertility, pregnancy, during pre- and postnatal development, appetite, pain-sensation, mood, and memory, and in mediating the pharmacological effects of cannabis.

Synthetic cannabinoids are compounds that have a cannabinoid-like structure and are manufactured using chemical means rather than by the plant.

Certain cannabinoids are described in more detail below.

Cannabidiol (CBD) is a major cannabinoid constituent of Cannabis species, such as the hemp plant (*Cannabis sativa*). Unlike other cannabinoids, such as THC, cannabidiol does not bind CB1 or CB2, or its binding to the receptors is negligible in terms of inducing a pharmacological effect. Thus, cannabidiol does not cause the central or peripheral nervous system effects mediated by the CB1 or CB2 receptors. CBD has little or no psychotropic (cannabimimetic) activity and its molecular structure and properties are substantially different from those of other cannabinoids.

CBD and CBDV administration have been the subject of research in an attempt to provide an alternative treatment for various diseases and disorders which may respond to such treatment.

There have been many studies done in animals to determine the metabolism of CBD and CBDV. The pharmacokinetics of CBD and CBDV are complex, mainly due to a substantial first pass effect. This in turn causes the bioavailability of oral CBD to be poor in humans and other species.

The most abundant metabolites of CBD are hydroxylated 7-carboxy derivatives of CBD which include: 2"-OH-7-COOOH,3",4",5"-trinor CBD; CBD-glucuronide; 4"-OH-7-COOH CBD; 2"-OH-7-COOH CBD; 10-OH-7-COOH CBD; 3"-OH-7-COOH CBD; 7-OH-3"-COOH,4",5"-dinor CBD; 7-COOH-8,9-dihydro-8,9-diOH CBD; 1"-OH-7-COOH CBD; 6-OH-42-COOH,5"-nor CBD; 6-OH-3"-COOH,4",5"-dinor CBD; 7-COOH CBD; 7-OH-4"-COOH, 5"-nor CBD; 4"-COOH,5"-nor CBD; 7-OH CBD; 8,9-dihydro-7,8,9-triOH CBD; cannabinol; 3"-COOH,4",5"-dinor CBD; 2"-COOH,3",4",5"-trinor CBD; 2", 6-diOH,3", 4",5"-trinor CBD6,7-diOH CBD; 7-OH-1"-COOH,2",3",4", 5"-tetranor CBD; 6-OH CBD; 7-OH-5"-COOH CBD;

1"-COOH,2",3",4",5"-tetranor CBD; 6-OH-1"-COOH,2", 3",4",5"-tetranor CBD and 6-OH-5"-COOH CBD (Ujvary and Hanus, 2016).

Although it is currently unknown which metabolites occur for the CBDV molecule, it is likely that similar metabolites exist for CBDV as for CBD, however the metabolites will have a propyl sidechain rather the pentyl sidechain which exists on the CBD molecule.

The U.S. Pat. No. 6,630,507 describes numerous analogues of cannabidiol. The compound 6-OH CBD is detailed in the document however there are no data presented to provide evidence that this compound may have any efficacy as a therapeutic agent.

Tetrahydrocannabinol (THC) is the principal psychoactive constituent of cannabis. THC is a partial agonist at the CB1 and CB2 receptors. Synthetic THC or dronabinol is approved for the treatment of loss of appetite in AIDS patients and nausea and vomiting caused by cancer chemotherapy.

Of the over 100 natural cannabinoids identified in *Cannabis sativa*, seven have been classified as CBD-type compounds, these cannabinoids have the same absolute configuration as CBD. These are: CBD, Cannabidiolic acid (CBDA), Cannabidivarin (CBDV), Cannabidivarin acid (CBDVA), Cannabidiol-C1 (CBD-C1), Cannabidiol-C4 (CBD-C4), Cannabidiol-C6 (CBD-C6) and Cannabidiol monomethyl ether (CBDM).

Cannabidiolic acid (CBDA) is the main form in which CBD exists in the cannabis plant. It is converted into CBD after decarboxylation.

Cannabidivarin (CBDV) is a homolog of CBD, with the sidechain shortened by two methylene bridges. CBDV is a non-psychoactive cannabinoid and has been shown to have anti-convulsant activity in a mouse model of epilepsy.

Cannabidiol-C1 (CBD-C1) also known as cannabidiorcol is a homolog of CBD, with the sidechain shortened by four methylene bridges. CBD-C1 occurs naturally in plants producing CBD but has not been shown to have any therapeutic effects.

Cannabidiol-C4 (CBD-C4) also known as nor-cannabidiol is a homolog of CBD, with the sidechain shortened by one methylene bridge. CBD-C4 occurs naturally in plants producing CBD and prior to the present invention has not been shown to have any therapeutic effects.

Cannabidiol-C6 (CBD-C6) is a homolog of CBD, with the sidechain increased by one methylene bridge. CBD-C6 may occur naturally in plants producing CBD and prior to the present invention has not been shown to have any therapeutic effects.

The present invention demonstrates data for the first time to indicate that the compound 6-hydroxy cannabidivarin may have therapeutic benefit.

BRIEF SUMMARY OF THE DISCLOSURE

In accordance with a first aspect of the present invention there is provided 6-hydroxy cannabidivarin (6-OH CBDV) for use as a medicament.

Preferably the 6-OH CBDV is present as a synthetic compound. Alternatively, the 6-OH CBDV is present as a pure and isolated compound.

Preferably the dose of 6-OH CBDV is greater than 100 mg/kg/day. More preferably the dose of 6-OH CBDV is greater than 250 mg/kg/day. More preferably the dose of 6-OH CBDV is greater than 500 mg/kg/day. More preferably the dose of 6-OH CBDV is greater than 750 mg/kg/day. More preferably the dose of 6-OH CBDV is greater than 1000 mg/kg/day. More preferably the dose of 6-OH CBDV is greater than 1500 mg/kg/day.

Alternatively, the dose of 6-OH CBDV is less than 100 mg/kg/day. More preferably the dose of 6-OH CBDV is less than 50 mg/kg/day. More preferably the dose of 6-OH CBDV is less than 20 mg/kg/day. More preferably the dose of 6-OH CBDV is less than 10 mg/kg/day. More preferably the dose of 6-OH CBDV is less than 5 mg/kg/day. More preferably the dose of 6-OH CBDV is less than 1 mg/kg/day. More preferably the dose of 6-OH CBDV is less than 0.5 mg/kg/day.

In accordance with a second aspect of the present invention there is provided a composition for use as a medicament comprising 6-hydroxy cannabidivarin (6-OH CBDV), and one or more pharmaceutically acceptable excipients.

In accordance with a third aspect of the present invention there is provided a 6-hydroxy cannabidivarin (6-OH CBDV) for use in the treatment of epilepsy. Preferably the epilepsy is treated in a mammal. More preferably the mammal is a human. Alternatively, the mammal is a dog.

In accordance with a fourth aspect of the present invention there is provided a method for the production of 6-hydroxy cannabidivarin (6-OH CBDV).

BRIEF DESCRIPTION OF THE DRAWINGS

Embodiments of the invention are further described hereinafter with reference to the accompanying drawings, in which:

FIG. 1 shows the effect of 6-OH CBDV in the MEST test in mouse.

The cannabinoids described in the present application are listed below along with their standard abbreviations.

CBD Cannabidiol

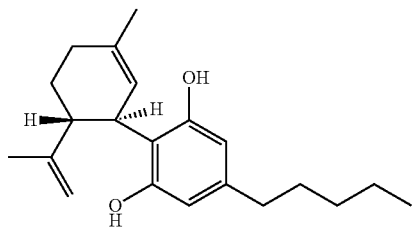 [SMILES: C=C(C)[C@@H]1CCC(C)=C[C@H]1c1c(O)cc(CCCCC)cc1O]

| | |
|---|---|
| 6-OH CBDV | Alpha 6-hydroxy cannabidivarin 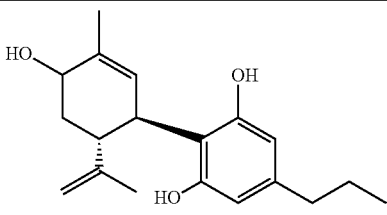 |

DETAILED DESCRIPTION

Example 1

Synthetic Production Method for Alpha 6-Hydroxy Cannabidivarin (6-OH CBDV)

As previously described the compound 6-OH CBDV is a metabolite of cannabidiol.

The synthetic pathway described below details a methodology that can be used in order to produce the cannabinoid alpha 6-OH CBDV.

On the scheme R=$C_3H_7$

To CBDV (5.00 g, 17.5 mmol) in anhydrous pyridine (20 mL) was added acetic anhydride (5.63 g, 5.20 mL, 55.2 mmol) and the solution was stirred for 4 h. Dichloromethane (300 mL) was added and the solution was washed with water (200 ml), 1M hydrochloric acid (200 mL), saturated aqueous sodium bicarbonate (200 mL), dried (MgSO4) and concentrated to give CBDV diacetate (6.84 g, quantitative), as a yellow oil which was used without further purification.

To CBDV diacetate (4.00 g, 10.8 mmol) in glacial acetic acid (9 mL) and acetic anhydride (4.96 g, 4.59 mL, 48.6 mmol) was added sodium dichromate (3.86 g, 13.0 mmol) and the mixture was stirred at room temperature for 4 days. The resulting solution was diluted with water (150 mL) and extracted with diethyl ether (2×150 mL). The combined organic extracts were washed with saturated aqueous sodium bicarbonate (150 mL), dried (MgSO4) and concentrated to give a yellow oil that was purified using a Biotage Isolera automated chromatography system under normal phase conditions (silica column, gradient of 5→33% ethyl acetate in petrol) with detection at 254 nm to give 6-oxo-CBDV diacetate (1.40 g 33%), as a colourless oil.

Rf=0.36 (ethyl acetate-petrol, 1:4 v/v)

To lithium aluminium hydride (0.58 g, 15.3 mmol) in diethyl ether (50 mL) at 0° C. was added 6-oxo-CBDV diacetate (1.40 g, 3.64 mmol) in diethyl ether (23 mL) and the mixture was stirred at room temperature for 4 h. The resulting mixture was cooled in an ice bath and cautiously quenched with iced water (100 mL). 1 M Hydrochloric acid (60 mL) was added and the mixture was extracted with diethyl ether (100 mL+50 mL). The combined organic layers were washed with saturated brine (100 mL), dried (MgSO4) and concentrated to give a pale yellow oil that was purified using a Biotage Isolera automated chromatography system under normal phase conditions (silica column, gradient of 7→53% ethyl acetate in petrol) with detection at 254 nm to give 6-oxo-CBDV (0.70 g, 64%), as a white glassy solid.

Rf=0.29 (ethyl acetate-petrol, 3:7 v/v)

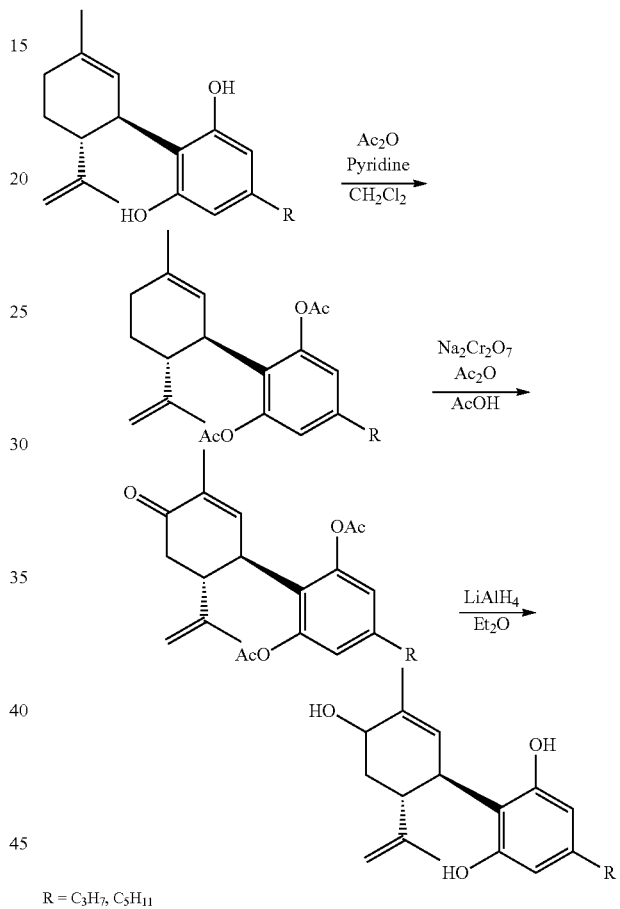

R = $C_3H_7$, $C_5H_{11}$

The resultant material was confirmed to be alpha 6-hydroxy-cannabidivarin (6-OH CBDV). The compound is a yellow glassy semi-solid material with the chemical formula $C_{19}H_{26}O_3$ and a molecular weight of 302.4 g/mol.

Purity of the compound was tested by HPLC which was shown to produce a 96.7% pure material.

6-OH CBDV was stored at −20° C. and protected from light until required for testing.

Example 2

Evaluation of 6-Hydroxy Cannabidivarin (6-OH CBDV) for Anticonvulsant Activity Using the Supramaximal Electroshock Seizure (Mes) Test in the Mouse The efficacy of 6-OH CBDV was tested in a mouse model of seizure, the supramaximal electroshock seizure (MES) test.

The supramaximal electroshock seizure (IVIES) test is widely utilized preclinically to evaluate anti-convulsant properties of molecules and standard anti-epileptic drugs (Loscher et al., 1991).

The MES test is a very stringent model in which mice receive a predetermined high-level electrical stimulus of sufficient intensity to reliably produce tonic hindlimb extensor seizures in 100% of control animals. As such the MES test is a rigorous evaluation of anticonvulsant activity (Swinyard, 1985).

Methods

Naïve mice were acclimatised to the procedure room in their home cages, with food and water available ad libitum.

Animals were dosed i.p. according to treatment group.

The vehicle (10 ml/kg i.p. 60 min pre-treatment time) was 1:1:18 vehicle 5% ethanol, 5% kolliphor EL, 90% saline.

The test compound, alpha 6-OH CBDV was prepared according to the method described in Example 1.

The test compound, 6-OH CBDV was administered at doses of 3, 10, 30, and 100 mg/kg given at 10 ml/kg i.p. 60 min pre-treatment time.

The positive control valproate was used at 250 mg/kg (10 ml/kg i.p. 30 min pre-treatment time).

Mice were individually assessed for the production of a tonic hind limb extensor seizure following a pre-determined high level (30 mA: 50 Hz) corneally delivered electroshock (0.2 sec duration) of sufficient intensity to reliably produce tonic hindlimb seizures in 100% of control animals.

Induction of seizure is measured as an all-or-nothing effect scored as either present (+) or absent (0) for each animal.

Data was collected by an observer unaware of the treatment for each animal and was expressed as the number of +'s or 0's for each treatment group.

The percentage inhibition of relevant vehicle treated group (the protection relative to vehicle treated controls) was then generated.

Significant differences between individual treatment groups and vehicle-treated groups were assessed using 2-tailed Fisher's Exact Probability test (p<0.05 considered significant).

Results

Table 1 below demonstrates the data produced in this experiment.

In the positive control valproate (250 mg/kg) treated group, administered i.p. 30 minutes before the test, all animals were scored as not having a seizure. This result was statistically significant (p<0.001) compared to the vehicle control.

In the 6-OH CBDV treatment groups, administered i.p. 60 minutes before the test, the dose of 3 and 10 mg/kg 6-OH CBDV only produced a 20% change in seizures compared to the vehicle control which was non-significant.

However, the doses of 30 and 100 mg/kg 6-OH CBDV enabled all mice to withstand seizures and produced a statistically significant effect compared to vehicle (p<0.001).

TABLE 1

Evaluation of effect of 6-OH CBDV in the MES test

| Treatment | Dose (mg/kg) | N | Pre-treatment time (mins) | % change from vehicle | Significance |
|---|---|---|---|---|---|
| Vehicle | — | 10 | 60 | — | — |
| Valproate | 250 | 10 | 30 | 100% | P < 0.001 |
| 6-OH CBDV | 3 | 10 | 60 | 20% | Non-significant |
| 6-OH CBDV | 10 | 10 | 60 | 20% | Non-significant |
| 6-OH CBDV | 30 | 10 | 60 | 100% | P < 0.001 |
| 6-OH CBDV | 100 | 10 | 60 | 100% | P < 0.001 |

Conclusions

These data demonstrate for the first time a therapeutic effect for the compound 6-OH CBDV.

These data are significant as they provide heretofore unknown evidence that this cannabinoid may be of therapeutic value.

Example 3

Evaluation of 6-Hydroxy Cannabidivarin (6-OH CBDV) for Anticonvulsant Activity Using the Maximal Electroshock Seizure Threshold (Mest) Test in the Mouse The efficacy of 6-OH CBDV was tested in a mouse model of generalised seizure, the maximal electroshock seizure threshold (MEST) test.

The maximal electroshock seizure threshold (MEST) test is widely utilized preclinically to evaluate pro- or anti-convulsant properties of test compounds (Loscher et al., 1991).

In the MEST test the ability of a drug to alter the seizure threshold current required to induce hind limb tonic extensor convulsions is measured according to an "up and down" method of shock titration (Kimball et al., 1957). An increase in seizure threshold is indicative of anti-convulsant effect. Antiepileptic drugs including the sodium channel blockers (e.g. lamotrigine) with clinically proven efficacy against generalised tonic-clonic seizures all exhibit anti-convulsant properties in this test in the mouse.

Conversely, a reduction in seizure threshold is indicative of a pro-convulsant effect as observed with known convulsant agents such as picrotoxin.

The ability of a test compound to alter the stimulus intensity, expressed as current (mA), required to induce the presence of tonic hind limb extensor convulsions, is assessed in the MEST. The outcome of the presence (+) or absence (0) of tonic hind limb extensor convulsions observed from a current to produce tonic hind limb extension in 50% of animals in the treatment group ($CC_{50}$) determines the seizure threshold for the treatment group and the effects were then compared to the $CC_{50}$ of the vehicle control group.

Methods

Study Details:

Naïve mice were acclimatised to the procedure room in their home cages for up to 7 days, with food and water available ad libitum.

All animals were weighed at the beginning of the study and randomly assigned to treatment groups based on a mean distribution of body weight across groups. All animals were dosed at 10 mL/kg via intraperitoneal (i.p) injection, with either vehicle, 6-OH CBDV at 3, 10 or 30 mg/kg, diazepam at 2.5 mg/kg or sodium valproate at 250 mg/kg.

Animals were individually assessed for the production of a tonic hind limb extensor convulsion at 15 min post-dose for vehicle, at 15, 15 and 30 min post-dose for 6-OH CBDV at 3, 10 and 30 mg/kg respectively, and 30 min post-dose for diazepam and sodium valproate, from a single electroshock.

The first animal within a treatment group was given a shock at the expected or estimated $CC_{50}$ current. For subsequent animals, the current was lowered or raised depending on the convulsions outcome from the preceding animal.

Data generated from each treatment group were used to calculate the $CC_{50} \pm SEM$ values for the treatment group.

Test Compounds:

Vehicle: (5% ethanol, 5% solutol, 90% Saline) was prepared as follows: 2 mL of ethanol, 2 mL of solutol were warmed to 60° C., in 36 mL of saline (1:1:18).

In the vehicle group, the $CC_{50}$ value was calculated to be 25.7 mA.

In the positive control diazepam (2.5 mg/kg) treated group, administered i.p. 30 minutes before the test, the $CC_{50}$ value was 57.5 mA. In the sodium valproate (250 mg/kg) treated group, administered i.p. 30 minutes before the test, the $CC_{50}$ value was 281.5 mA. These results were statistically significant (p<0.001) compared to the vehicle control.

In the 6-OH CBDV treatment groups, administered i.p. 15, 15, and 30 minutes before the test, the doses of 3, 10 and 30 mg/kg 6-OH CBDV produced a statistically significant $CC_{50}$ value compared to vehicle at all three doses of the compound.

Such data are indicative that this compound will be of therapeutic benefit.

TABLE 2

Evaluation of effect of 6-OH CBDV in the MEST test

| Treatment | Dose (mg/kg) | N | Pre-treatment time (mins) | $CC_{50} \pm SEM$ | % change from vehicle | Significance |
|---|---|---|---|---|---|---|
| Vehicle | — | 12 | 15 | 25.7 ± 0.4 | — | — |
| Diazepam | 2.5 | 12 | 30 | 57.5 ± 0.3 | 124% | P < 0.001 |
| Sodium Valproate | 250 | 12 | 30 | 281.5 ± 5.8 | 997% | P < 0.001 |
| 6-OH CBD | 3 | 12 | 15 | 54.2 ± 1.4 | 111% | P < 0.001 |
| 6-OH CBD | 10 | 12 | 15 | 63.5 ± 3.4 | 147% | P < 0.001 |
| 6-OH CBD | 30 | 12 | 30 | 92.5 ± 0.4 | 260% | P < 0.001 |

Positive controls: diazepam was used at 2.5 mg/kg and sodium valproate at 250 mg/kg.

The test compound, alpha 6-OH CBDV was prepared according to the method described in Example 1. 6-OH CBDV was administered at 3, 10 and 30 mg/kg (i.p.) in a 1:1:18 ethanol:soluto:0.9% saline formulation.

Sample Collection:

Each animal was humanely killed immediately after production of a convulsion by destruction of the brain from striking the cranium, followed by the confirmation of permanent cessation of the circulation from decapitation under The Humane Killing of Animals under Schedule 1 to the Animals (Scientific Procedures) Act 1986. Terminal blood and brain collection were performed following decapitation.

Blood was collected in Lithium-heparin tubes and centrifuged at 4° C. for 10 minutes at 1500× g. The resulting plasma was removed (>100 μL) and split into 2 aliquots of 0.5 mL Eppendorf tubes containing 100 μL of ascorbic acid (100 mg/mL) for stabilisation. Brains were removed, washed in saline and halved. Each half was placed into separate 2 mL screw cap cryovials, weighed and frozen on cardice.

Statistical Analysis

The data for each treatment group were recorded as the number of +'s and 0's at each current level employed and this information is then used to calculate the $CC_{50}$ value (current required for 50% of the animals to show seizure behaviour)±standard error.

6-OH CBDV effects were also calculated as percentage change in $CC_{50}$ from the vehicle control group.

Significant difference between drug-treated animals and controls were assessed according to Litchfield and Wilcoxon (1949).

Results

Table 2 below demonstrates the data produced in this experiment, and FIG. 1 illustrates these results.

Conclusions

6-OH CBDV produced a dose-related increase in MEST, which provides evidence that this compound exhibits anti-convulsive properties. Significant effects were observed at 3, 10, and 30 mg/kg, when compared to vehicle.

These data are significant as they provide heretofore unknown evidence that this cannabinoid may be of therapeutic value.

The invention claimed is:

1. A method of treating epilepsy in a subject in need thereof, comprising administering a therapeutically effective dose of 6-hydroxy cannabidivarin (6-OH CBDV) to the subject.

2. The method of claim 1, wherein the 6-OH CBDV is in the form of a synthetic compound.

3. The method of claim 1, wherein the 6-OH CBDV is in the form of a pure or isolated compound.

4. The method of claim 1, wherein the dose of 6-OH CBDV is greater than 100 mg/kg/day.

5. The method of claim 1, wherein the dose of 6-OH CBDV is less than 100 mg/kg/day.

6. The method of claim 1, wherein the subject is a mammal.

7. The method of claim 6, wherein the mammal is a human.

8. The method of claim 6, wherein the mammal is a dog.

9. The method of claim 1, wherein the dose of 6-OH CBDV is less than 10 mg/kg/day.

10. The method of claim 1, wherein the dose of 6-OH CBDV ranges from 10 mg/kg/day to 100 mg/kg/day.

11. The method of claim 1, wherein the dose of 6-OH CBDV ranges from 20 mg/kg/day to 100 mg/kg/day.

12. The method of claim 1, wherein the dose of 6-OH CBDV ranges from 50 mg/kg/day to 100 mg/kg/day.

13. The method of claim 1, wherein the dose of 6-OH CBDV ranges from greater than 100 mg/kg/day to 1500 mg/kg/day.

14. The method of claim 1, wherein the dose of 6-OH CBDV ranges from greater than 100 mg/kg/day to 1000 mg/kg/day.

15. The method of claim 1, wherein the dose of 6-OH CBDV ranges from greater than 100 mg/kg/day to 750 mg/kg/day.

16. The method of claim 1, wherein the dose of 6-OH CBDV ranges from greater than 100 mg/kg/day to 500 mg/kg/day.

17. The method of claim 1, wherein the treatment comprises producing an anticonvulsive effect in the subject.

18. The method of claim 1, wherein the treatment reduces seizures in the subject or increases a threshold of seizures in the subject, compared to a control.

19. The method of claim 1, wherein the treatment comprises treating tonic seizures and/or tonic-clonic seizures.

20. The method of claim 1, wherein the 6-OH CBDV is at least 96.7% pure as measured by HPLC.

* * * * *